US009449241B2

(12) United States Patent
Hager et al.

(10) Patent No.: US 9,449,241 B2
(45) Date of Patent: Sep. 20, 2016

(54) SYSTEM AND METHOD FOR DETECTING AND TRACKING A CURVILINEAR OBJECT IN A THREE-DIMENSIONAL SPACE

(75) Inventors: Gregory Donald Hager, Baltimore, MD (US); Nicolas Padoy, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 307 days.

(21) Appl. No.: 13/985,815

(22) PCT Filed: Feb. 23, 2012

(86) PCT No.: PCT/US2012/026348
§ 371 (c)(1),
(2), (4) Date: Aug. 15, 2013

(87) PCT Pub. No.: WO2012/116198
PCT Pub. Date: Aug. 30, 2012

(65) Prior Publication Data
US 2013/0329038 A1 Dec. 12, 2013

Related U.S. Application Data

(60) Provisional application No. 61/445,621, filed on Feb. 23, 2011.

(51) Int. Cl.
*G06K 9/00* (2006.01)
*G06K 9/32* (2006.01)
*B25J 9/16* (2006.01)

(52) U.S. Cl.
CPC ............ *G06K 9/3241* (2013.01); *B25J 9/1697* (2013.01); *G05B 2219/39123* (2013.01); *G05B 2219/4705* (2013.01); *Y10S 901/46* (2013.01)

(58) Field of Classification Search
CPC .................................................. G06K 9/3241

USPC ......................................................... 348/141
See application file for complete search history.

(56) References Cited

U.S. PATENT DOCUMENTS 6,529,617 B1    3/2003  Prokoski
6,795,567 B1 *  9/2004  Cham ................... G06T 7/2033
                                                          382/103

(Continued)

FOREIGN PATENT DOCUMENTS

WO    WO-2007/111955 A2    4/2007

OTHER PUBLICATIONS

International Search Report and Written Opinion of PCT/US2012/026348.

(Continued)

*Primary Examiner* — Jeffery Williams
(74) *Attorney, Agent, or Firm* — Venable LLP; Henry J. Daley; Laura G. Remus

(57) ABSTRACT

A system for detecting and tracking a curvilinear object in a three-dimensional space includes an image acquisition system including a video camera arranged to acquire a video image of the curvilinear object and output a corresponding video signal, the video image comprising a plurality n of image frames each at a respective time $t_i$, where i=1, 2, . . . , n; and a data processing system adapted to communicate with the image acquisition system to receive the video signal. The data processing system is configured to determine a position, orientation and shape of the curvilinear object in the three-dimensional space at each time $t_i$ by forming a computational model of the curvilinear object at each time $t_i$ such that a projection of the computation model of the curvilinear object at each time ti onto a corresponding frame of the plurality of image frames of the video image matches a curvilinear image in the frame to a predetermined accuracy to thereby detect and track the curvilinear object from time $t_i$ to time $t_n$.

19 Claims, 9 Drawing Sheets

(56) References Cited

U.S. PATENT DOCUMENTS

| | | | |
|---|---|---|---|
| 7,386,339 B2 | 6/2008 | Strommer et al. | |
| 2006/0279630 A1* | 12/2006 | Aggarwal | G01S 3/7864 348/143 |
| 2007/0238981 A1 | 10/2007 | Zhu et al. | |
| 2008/0171936 A1 | 7/2008 | Homan et al. | |
| 2009/0088634 A1 | 4/2009 | Zhao et al. | |
| 2009/0175541 A1* | 7/2009 | Bensimon | G06K 9/4633 382/203 |
| 2010/0195869 A1* | 8/2010 | Geiss | G06K 9/00369 382/103 |

OTHER PUBLICATIONS

Amini et al., "Snakes and splines for tracking non-rigid heart motion," in ECCV, 1996, pp. 251-261.

Bartoli et al.,"Generalized thin-plate splinewarps," in CVPR, 2007.

Cham et al., "Stereo coupled active contours," Computer Vision and Pattern Recognition, IEEE Computer Society Conference on, vol. 0, p. 1094, 1997.

Frangi et al., "Multiscale vessel enhancement filtering," in MIC-CAI, 1998, pp. 130-137.

Geigeret al., "Dynamic programming for detecting, tracking, and matching deformable contours," PAMI, vol. 17, No. 3, pp. 294-302, 1995.

Glocker et al., "Dense image registration through mrfs and efficient linear programming," Medical Image Analysis, vol. 12, No. 6, pp. 731-741,2008.

Heibel et al., "Discrete tracking of parametrized curves," in CVPR, 2009.

Isard et al., "Condensation—conditional density propagation for visual tracking," IJCV, vol. 29, No. 1, pp. 5-28, 1998.

Javdani et al., "Modeling and perception of deformable one-dimensional objects," in ICRA, 2011, pp. 1607-1614.

Kass et al., "Snakes: Active contour models," IJCV, vol. 1, No. 4, pp. 321-331, 1988.

Komodakis et al., "Fast, approximately optimal solutions for single and dynamic mrfs," in CVPR, 2007.

Mayeret al., "A system for robotic heart surgery that learns to tie knots using recurrent neural networks," in IROS, 2006, pp. 543-548.

Padoy et al., "3d thread tracking for robotic assistance in telesurgery," in IROS, 2011, pp. 2102-2107.

Padoy et al., "Human-Machine Collaborative Surgery Using Learned Models". To appear in the proceedings of the International Conference on Robotics and Automation (ICRA).

Shechteret al., "Temporal tracking of 3D coronary arteries in projection angiograms," in Medical Imaging, vol. 4684. SPIE, 2002.

van den Berg et al., "Superhuman performance of surgical tasks by robots using iterative learning from human-guided demonstrations," in ICRA, 2010, pp. 20742081.

Wang et al., "Robust guidewire tracking in fluoroscopy," in CVPR, 2009, pp. 691-698.

* cited by examiner

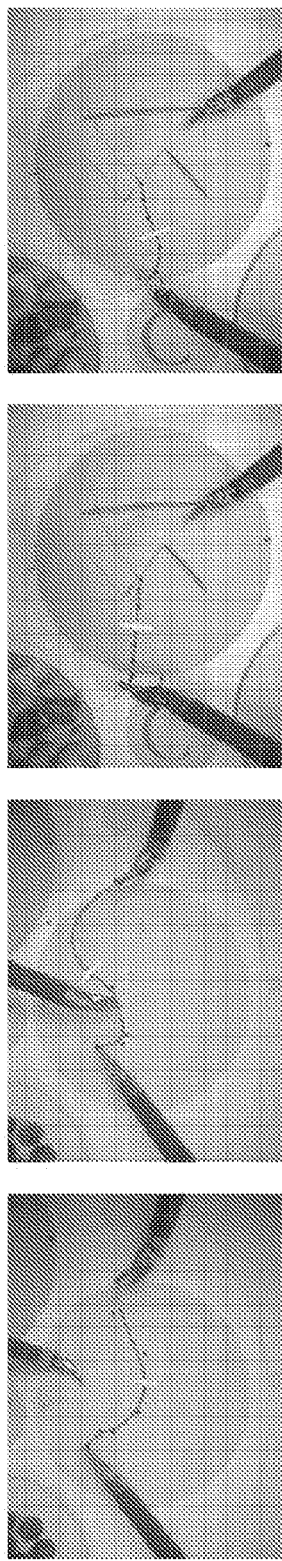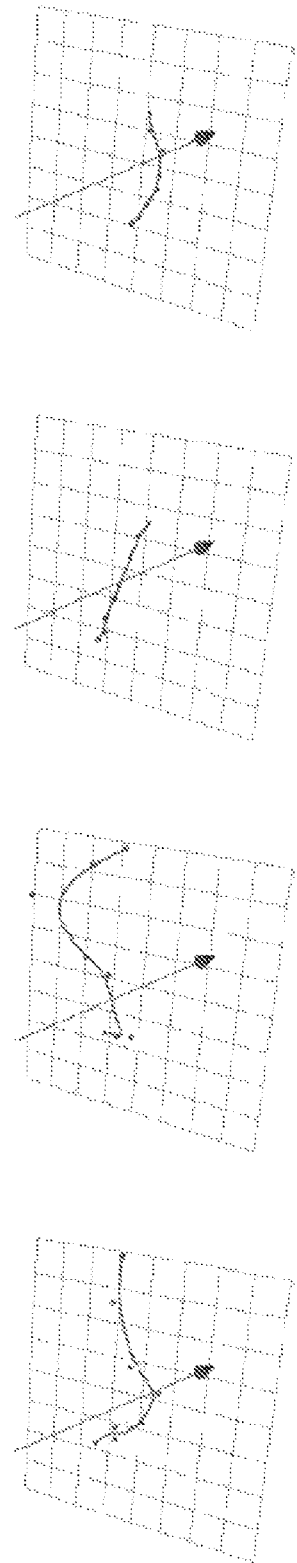
FIG. 6A
FIG. 6B

SYSTEM AND METHOD FOR DETECTING AND TRACKING A CURVILINEAR OBJECT IN A THREE-DIMENSIONAL SPACE

CROSS-REFERENCE OF RELATED APPLICATION

This is a national stage application under 35 U.S.C. §371 of PCT/US2012/026348 filed Feb. 23, 2012, the entire contents of which are incorporated herein by reference and that claims priority to U.S. Provisional Application No. 61/445,621 filed Feb. 23, 2011, the entire contents of which are hereby incorporated by reference.

This invention was made with U.S. Government support of Grant No. CPS 0931805, awarded by NSF. The U.S. Government has certain rights in this invention.

BACKGROUND

1. Field of Invention

The field of the currently claimed embodiments of this invention relates to systems and methods for detecting and tracking objects, and more particularly to systems and methods for detecting and tracking a curvilinear object in a three-dimensional space.

2. Discussion of Related Art

Many dexterous tasks involve the manipulation of deformable 3-dimensional (3D) curvilinear objects. Examples of such objects are sutures in surgery, catheters in interventional radiology and wires in maintenance tasks. Developing robotic assistance systems for such tasks requires the accurate localization and tracking of the curvilinear structures present in the scene. Contrary to the tracking of contours, which has been much addressed in the computer vision community [1]-[5], the tracking of purely curvilinear structures has received less attention. (The references cited in square brackets are listed at the end for convenience.) This is especially the case for open curves in a 3D setting. Related work in this area mainly comes from the medical imaging community, where vessels [6] or catheters [7], [8] need to be localized in angiographic images. In these cases, the displacements and deformations are constrained by the human anatomy. The free manipulation of an object such as a thread is, however, less constrained and larger deformations can occur. Moreover, as opposed to contours, purely curvilinear objects do not have any stable side and are usually more flexible. There thus remains a need for improved systems and methods for detecting and tracking curvilinear objects.

SUMMARY

A system for detecting and tracking a curvilinear object in a three-dimensional space according to an embodiment of the current invention includes an image acquisition system including a video camera arranged to acquire a video image of the curvilinear object and output a corresponding video signal, the video image comprising a plurality n of image frames each at a respective time $t_i$, where $i=1, 2, \ldots, n$; and a data processing system adapted to communicate with the image acquisition system to receive the video signal. The data processing system is configured to determine a position, orientation and shape of the curvilinear object in the three-dimensional space at each time $t_i$ by forming a computational model of the curvilinear object at each time $t_i$ such that a projection of the computation model of the curvilinear object at each time $t_i$ onto a corresponding frame of the plurality of image frames of the video image matches a curvilinear image in the frame to a predetermined accuracy to thereby detect and track the curvilinear object from time $t_1$ to time $t_n$.

A robotic system according to an embodiment of the current invention includes a manipulator assembly, a manipulator control system configured to communicate with the manipulator assembly, and a system for detecting and tracking a curvilinear object in a three-dimensional space configured to communicate with the manipulator control system. The system for detecting and tracking a curvilinear object in a three-dimensional space includes an image acquisition system comprising a video camera arranged to acquire a video image of the curvilinear object and output a corresponding video signal, the video image comprising a plurality n of image frames each at a respective time $t_i$, where $i=1, 2, \ldots, n$; and a data processing system adapted to communicate with the image acquisition system to receive the video signal. The data processing system is configured to determine a position, orientation and shape of the curvilinear object in the three-dimensional space at each time $t_i$ by forming a computational model of the curvilinear object at each time $t_i$ such that a projection of the computation model of the curvilinear object at each time $t_i$ onto a corresponding frame of the plurality of image frames of the video image matches a curvilinear image in the frame to a predetermined accuracy to thereby detect and track the curvilinear object from time $t_1$ to time $t_n$.

A method for detecting and tracking a curvilinear object in a three-dimensional space according to an embodiment of the current invention includes receiving, by a data processing system, a video signal from an image acquisition system that comprises a video camera arranged to acquire a video image of the curvilinear object and output the video signal, the video image including a plurality n of image frames each at a respective time $t_i$, where $i=1, 2, \ldots, n$; and determining a position, orientation and shape of the curvilinear object in the three-dimensional space at each time $t_i$ by forming a computational model of the curvilinear object at each time $t_i$ using the data processing system such that a projection of the computation model of the curvilinear object at each time $t_i$ onto a corresponding frame of the plurality of image frames of the video image matches a curvilinear image in the frame to a predetermined accuracy to thereby detect and track the curvilinear object from time $t_i$ to time $t_n$.

A computer-readable medium according to an embodiment of the current invention includes computer-executable code for detecting and tracking a curvilinear object in a three-dimensional space. The computer-executable code includes instructions that, when executed by the computer, causes the computer to receive a video signal from an image acquisition system that includes a video camera arranged to acquire a video image of the curvilinear object and output the video signal, the video image including a plurality n of image frames each at a respective time $t_i$, where $i=1, 2, \ldots, n$; and determine a position, orientation and shape of the curvilinear object in the three-dimensional space at each time $t_i$ by forming a computational model of the curvilinear object at each time $t_i$ such that a projection of the computation model of the curvilinear object at each time $t_i$ onto a corresponding frame of the plurality of image frames of the video image matches a curvilinear image in the frame to a predetermined accuracy to thereby detect and track the curvilinear object from time $t_1$ to time $t_n$.

BRIEF DESCRIPTION OF THE DRAWINGS

Further objectives and advantages will become apparent from a consideration of the description, drawings, and examples.

FIG. 3A: The texture anchors the model (dotted line) on the object (continuous line). FIG. 3B: The texture highlights the difference between the two planar 3D configurations represented by continuous and dotted lines.

FIG. 4A: NURBS curve with four control points and corresponding MRF chain below. FIG. 4B: Exemplary discrete label set L. The spheres indicate the allowed 3D displacements from the center.

FIGS. 6A and 6B provide an example of tracking on two sequences, using a unicolor thread and tool position information (see [13] for more details). FIG. 6A: Reprojected spline C with control points and indication of the center. FIG. 6B: Different 3D view of spline C.

DETAILED DESCRIPTION

Figure 1:
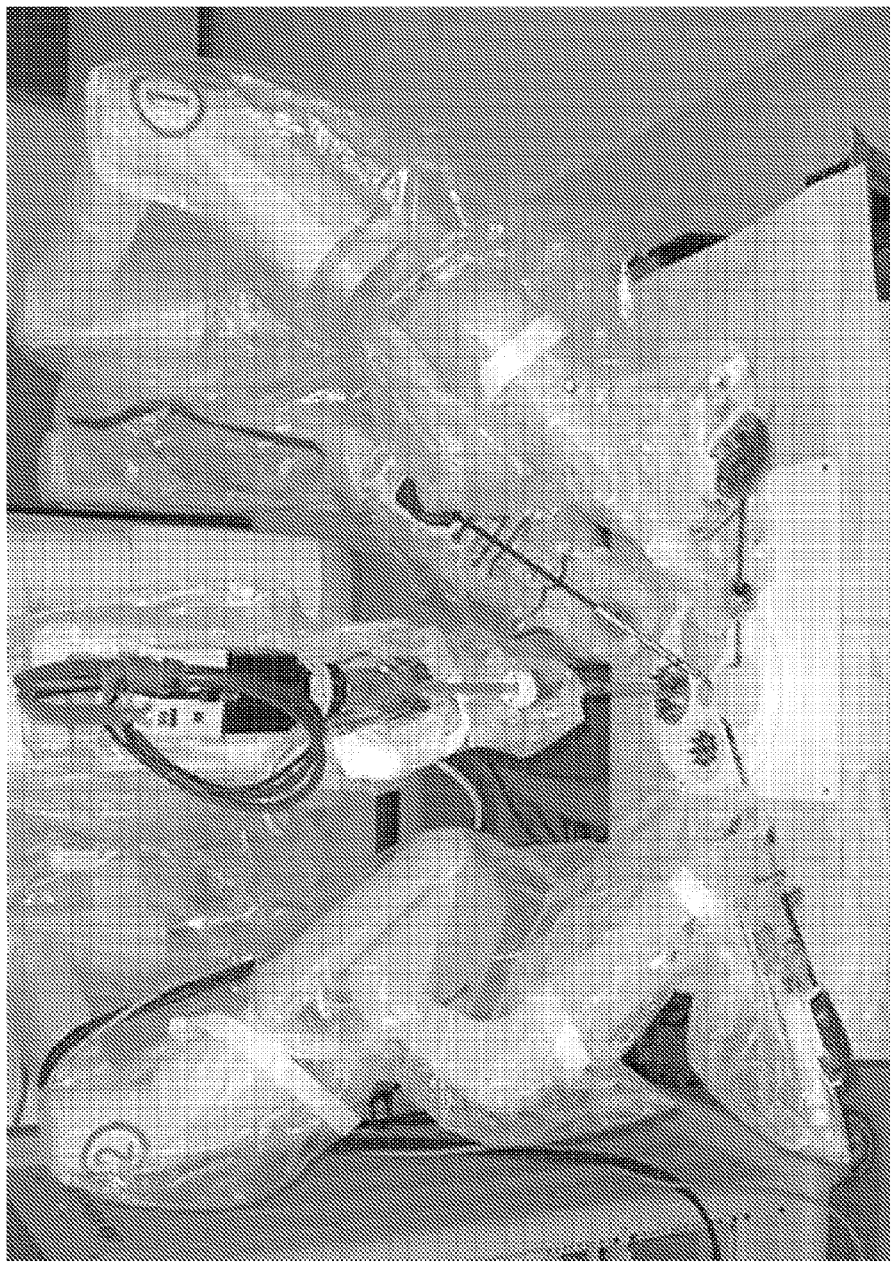
FIG. 1 is an example of a system setup showing the four robotic arms of a da Vinci tele-surgical robot according to an embodiment of the current invention. Three arms hold instruments and the fourth arm (center) holds a stereo endoscopic camera.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Some embodiments of the current invention extend telerobotic systems with automatic robotic primitives. Such a primitive consists of actions performed automatically by one or more robotic arms that can involve interaction with the physical environment. The primitives can be triggered manually, by voice command, or automatically using a contextual recognition system. Components of the primitives and coordination thereof may be triggered by recognizing motions or gestures that are part of the task being performed by the operator. Methods for visual tracking of task elements such as suture thread are also included in some embodiments of the current invention. Some embodiments of the current invention can provide an assistive primitive that includes an automatic detection and cutting of a thread by an autonomous robotic arm, for example.

Some embodiments of the current invention can reduce the workload of an operator of telerobotic systems, for example, thereby providing the operator with a system with improved ergonomics and usability. The system may also provide operators with capabilities that they would otherwise be unable to perform. An embodiment of the current invention can provide a solution to the problem of detecting and tracking a thread in 3D from stereo/mono cameras as well as methods for performing shared control of a robot, including vision-based shared control.

Some embodiments of the current invention can provide:
1) A robotic system with robotic arm(s) automatically controlled to assist a user tele-operating other robotic arms,
2) 3D thread tracking, and
3) Using a thread with color-patterns and color encoding for accurate 3D tracking. However, the broad concepts of the current invention are not limited to these particular examples.

Further embodiments of the current invention can include:
1) Automatic primitive triggering provided by recognized context (see, HUMAN-MACHINE COLLABORATIVE ROBOTIC SYSTEMS, International Application No PCT/US2011/060638, the entire contents of which are incorporated herein by reference),
2) Additional ergonomic improvement through voice control,
3) Use of shape deformation priors to improve tracking,
5) Extension to rigid curvilinear objects, including using color coding, as well as using color patterns both on a needle and thread of a suture in one application,
6) If the thread is non-extensible, the method can be extended to using a single video-camera, and
7) The thread tracking approach can be used in non-robotic environments.

More generally, some embodiments of the current invention are directed to a system for detecting and tracking a curvilinear object in a three-dimensional space. The term "curvilinear object" is intended to refer to objects that are primarily one-dimensional structures, for example, in which one dimension is substantially greater than the other two. For example, one dimension may be a factor of 5 greater, or a factor of 10 greater, or even a factor of 100, or more, greater. A piece of thread or suture is an example of a curvilinear object. Thread will also be referred to as a deformable curvilinear object since it is free to make sharp bends, loops, and even crossing over portions such as when it is tied into a knot. Other examples can include wire, cord, fiber, optical fiber, rods, and the like. Even structured objects such as catheters, pipes, tubes, co-axial cables, etc. can be considered to be curvilinear objects in some applications. These are examples and are not intended to limit the scope of the invention.

The system for detecting and tracking a curvilinear object in a three-dimensional space according to some embodiments of the current invention includes an image acquisition system that includes a video camera arranged to acquire a video image of the curvilinear object and output a corresponding video signal. The video image includes a plurality n of image frames, each at a respective time $t_i$, where $i=1, 2, \ldots, n$. The number n can be a large number, especially if several frames per second are acquired, and if the tracking is over an extended period of time.

The system for detecting and tracking the curvilinear object also includes a data processing system adapted to communicate with the image acquisition system to receive the video signal. The data processing system can be a computer, such as, but not limited to, a laptop computer, desk top computer, a work station, a multiprocessor computer, a distributed computer system, such as networked computer, or any other suitable computing system. The data processing system can be a programmable system, and/or a special purpose system such as an ASIC and/or FPGA, for example. The data processor can also include memory devices and be in communication with data storage devices.

The data processing system is configured to determine a position, orientation and shape of the curvilinear object in the three-dimensional space at each time $t_i$ by forming a computational model of the curvilinear object at each time $t_i$ such that a projection of the computation model of the curvilinear object at each time $t_i$ onto a corresponding frame of the plurality of image frames of the video image matches a curvilinear image in the frame to a predetermined accuracy to thereby detect and track the curvilinear object from time $t_1$ to time $t_n$. The term "shape of the curvilinear object" is intended to refer to a curvilinear object having one or more bends along its length, for example. For example, a piece of thread can be bent, cured, looped, or even tied, thus exhibiting a wide range of different "shapes". Each time the thread takes on a different configuration, it can be viewed as taking on a different shape. As indicated above, the invention is not limited to only thread, but this example is useful for describing some concepts of the current invention.

Some particular embodiments for achieving the detection and tracking will be described in more detail below. However, the general concepts of the current invention are not limited to these particular embodiments. For example, as will be described in more detail below, the computational model can be, but is not limited to, a non-uniform rational B-spline model.

In some embodiments, the curvilinear object can have a texture that is visible in the video image and the data processing system can be further configured to determine the texture of the curvilinear object in the three-dimensional space at each time $t_i$ by including texture in the computational model of the curvilinear object at each time $t_i$. The term "texture" of the curvilinear object is intended to refer to any features of the curvilinear object that are visible by the video camera and which allow at least one portion of the curvilinear object to be distinguished from at least one other portion based on a difference in the texture. The term "visible" can be for imaging in visible or non-visible portions of the electromagnetic spectrum, as long as the video camera is suitable for imaging at the desired wavelengths. Some examples of texture can include, but are not limited to, differences in color or shade, differences in roughness (or smoothness), different surface structures, markings or tags, etc. Objects can naturally have textures that can be used by the system, or objects can be modified to include a texture, for example, but not limited to, adding a color pattern to a curvilinear object.

In some embodiments, the curvilinear object can have a substantially invariant length and the computational model of the curvilinear object can include a constant-length constraint on the modeled curvilinear object. Substantially invariant means that any change in length in the particular application can be ignored. For example, thread can be stretched, particularly if enough stretching force is applied, but for many uses of thread the amount of stretching is not of concern.

In some embodiments, the video camera can be a stereo video camera arranged to acquire a stereo video image of the curvilinear object and output a corresponding stereo video signal. In this case, the stereo video image includes a plurality n stereo pairs of image frames each at a respective time $t_i$, where i=1, 2, . . . , n. The data processing system is adapted to communicate with the image acquisition system to receive the stereo video signal.

The data processing system is configured to determine a position, orientation and shape of the curvilinear object in the three-dimensional space at each time $t_i$ by forming a computational model of the curvilinear object at each time $t_i$ such that a projection of the computation model of the curvilinear object at each time $t_i$ onto a corresponding stereo pair of frames of the plurality of stereo pairs of image frames of the stereo video image matches a two-dimensional curvilinear image in the stereo pair of frames to a predetermined accuracy to thereby detect and track the curvilinear object from time $t_1$ to time $t_n$.

Another embodiment of the current invention is directed to a robotic system that includes a manipulator assembly, a manipulator control system configured to communicate with the manipulator assembly, and a system for detecting and tracking a curvilinear object in a three-dimensional space configured to communicate with the manipulator control system. The robotic system can be a manufacturing robotic system, a maintenance robotic system, or a surgical robotic system, for example. The term "robotic system" is intended to include both fully automated as well as partially automated robotic systems. However, the invention is not limited to these particular examples. FIG. 1 shows an example of a surgical robotic system according to an embodiment of the current invention. A robotic system according to some embodiments of the current invention can include any of the systems for detecting and tracking a curvilinear object in a three-dimensional space described herein.

In some embodiments, the manipulator assembly can include at least one manipulator arm. Often, the manipulator assembly will include two, three, four or more manipulator arms. Each manipulator arm can have one or more manipulators or tolls attached thereto. The tools, for example, can be exchangeable tools in some embodiments.

In some embodiments, the data processing system can be further configured to receive information concerning a location of at least a portion of the manipulator arm from the manipulator control system to be used in determining the position, orientation and shape of the curvilinear object in the three-dimensional space at each time $t_i$. The manipulator control system can be configured to receive information concerning at least one of the position, orientation or shape of the curvilinear object from the system for detecting and tracking the curvilinear object to at least help guide the manipulator arm to perform an automated or semi-automated task on the curvilinear object.

Methods of processing video signals and computer readable media encoded with instructions for processing video signals to detect and track curvilinear objects are also included in further embodiments of the current invention.

The following will describe some embodiments in more detail, but the general concepts of the current invention are not limited to these particular examples. The following examples focus on tracking a thread in a surgical setting. The general concepts of the current invention are not limited to this example which is used to help explain some concepts of the current invention.

Thread tracking can potentially be used for robotic assistance during an operation, for instance for visual serving during its robotic manipulation, or to perform length measurements. It can also be used for skills evaluation during the training of an operator. Typical surgical tasks involving thread manipulation are suturing and knot tying. Even though efforts towards robotic knot tying exist [9], [10], none of these approaches tracks the thread. This is indeed a very difficult problem, since the thread can deform in different directions with high speed and also undergo multiple occlusions.

The following examples according to an embodiment of the current invention illustrate the tracking of the thread with an assistance primitive, namely automatic scissors during tele-operation. (See FIG. 1 for an example of a setup.) Supposing that the thread is held between two instruments, by recovering the deformation of the thread while the instruments are moved, a third robotic instrument equipped with scissors can automatically come and cut it. Such a command could for instance be triggered by voice command.

Tracking a unicolor thread in 3D from images is ambiguous. Indeed, if parts of the thread are lying within a plane containing the camera center, different 3D configurations can produce the same visual perception. When an additional camera (stereo system) is used, ambiguities may arise for parts of the thread that lie within an epipolar plane. Therefore, according to an embodiment of the current invention texture is added to the thread with a pattern of multiple alternating colors to further reduce the number of ambiguous cases. First, the pattern has an advantage of anchoring the tracking model on the real thread. This provides the possibility of tracking only a portion of the thread. Second, length constraints provided by each color segment provide as many additional constraints on the deformations. Third, ambiguities due to planar configurations are then localized within the unicolor portions of the pattern. In the absence of (self-) occlusions, constraints on the length and on the smoothness of the thread address most of these ambiguities in practical situations, as long as the pattern is chosen such that the maximum length of each color segment is small enough not to allow for multiple bends of the thread within this segment.

Two-dimensional texture information is often used to estimate the deformation of surfaces [11]. We show in this example that 1D texture information can be successfully used together with curvilinearity constraints to track 1D deformable objects, using a single or two cameras. An alternative approach to recover the thread deformation is to model or learn the material properties of the thread [12]. They can serve as constraints to disambiguate between different possible thread configurations. A major difficulty in extending such an approach to a real tracking scenario is however the need to model physical contacts between the thread and the other objects, as well as to detect them in real time.

In this example, we model the thread as a non-uniform rational B-spline (NURBS). The projective invariance property of NURBS is used to compute the 2D projected curves from the 3D curve (and vice-versa) by considering solely the control points. The tracking problem is then formulated as an energy minimization problem over the spline parameters. The energy includes three terms defined to enforce the curvilinear appearance and length properties of the object.

We use a discrete approach [13] to minimize this energy and compare it to a gradient-based method. We extend the approach in [8], where a catheter is tracked in 2-dimensional (2D) fluoroscopic images, to 3D tracking from stereo. We also use an adaptive set of labels to obtain a tracking that is scalable to motions of different speeds.

The tracking is first evaluated off-line with synthetic data where the ground truth is available and also qualitatively with real data. In both cases, the thread is undergoing large deformations. Finally, the approach has been implemented on a real system based on a non-commercial version of the da Vinci robot from Intuitive Surgical™, in order to demonstrate an automatic scissors command.

METHODS

Setup

The scene, containing the thread is observed with a stereo camera system, as shown in FIG. 1. The two cameras are assumed to be calibrated. In the following, we denote their projection matrices by $P_i \in \mathbb{R}^{3 \times 4}$, $i \in \{1,2\}$. The last row of these matrices is denoted by $P_i^{(3)}$. While the tracking approach is presented in a stereo scenario, note however that the same approach is applicable to a mono-camera scenario by removing all terms related to the second camera. In this situation, it only requires a 3D initialization of the thread.

Thread Modeling

1) Parameterization: We model the thread in 3D using non-uniform rational B-splines [14], for their projective invariance property. This modeling allows us to work conveniently with parameterizations of either the 3D thread or of its 2D projections A NURBS curve C(Q,W,u) of degree d is defined as a linear combination of a set of control points $Q=\{Q_k\}_{k \in \{1,k\}}$ with weights $W=\{w_k\}$:

$$C(Q, W, u) = \sum_{k=1}^{K} R_{k,d}(u) Q_k, \quad u \in [0, 1], \tag{1}$$

where u is the curve parameter and $R_{k,d}$ are the rational basis functions [14]:

$$R_{k,d}(u) = \frac{N_{k,d}(u) w_k}{\sum_{i=1}^{K} N_{i,d}(u) w_i}, \quad u \in [0, 1], \tag{2}$$

The functions $N_{k,d}$ are the usual spline basis functions. If C(Q,W,u) represents a 3D curve, with Q a set of 3D points in homogeneous coordinates expressed as $Q_k^{3D}=[q_k 1]^T \in \mathbb{R}^4$, the projective invariance property of NURBS is expressed as follows for $i \in \{1,2\}$.

$$\begin{cases} P_i(C(Q, W, u)) = C(P_i(Q), V_i, u) \\ v_{i,k} = w_k, P_i^{(3)} \begin{bmatrix} q_k \\ 1 \end{bmatrix}. \end{cases} \tag{3}$$

Figure 2:
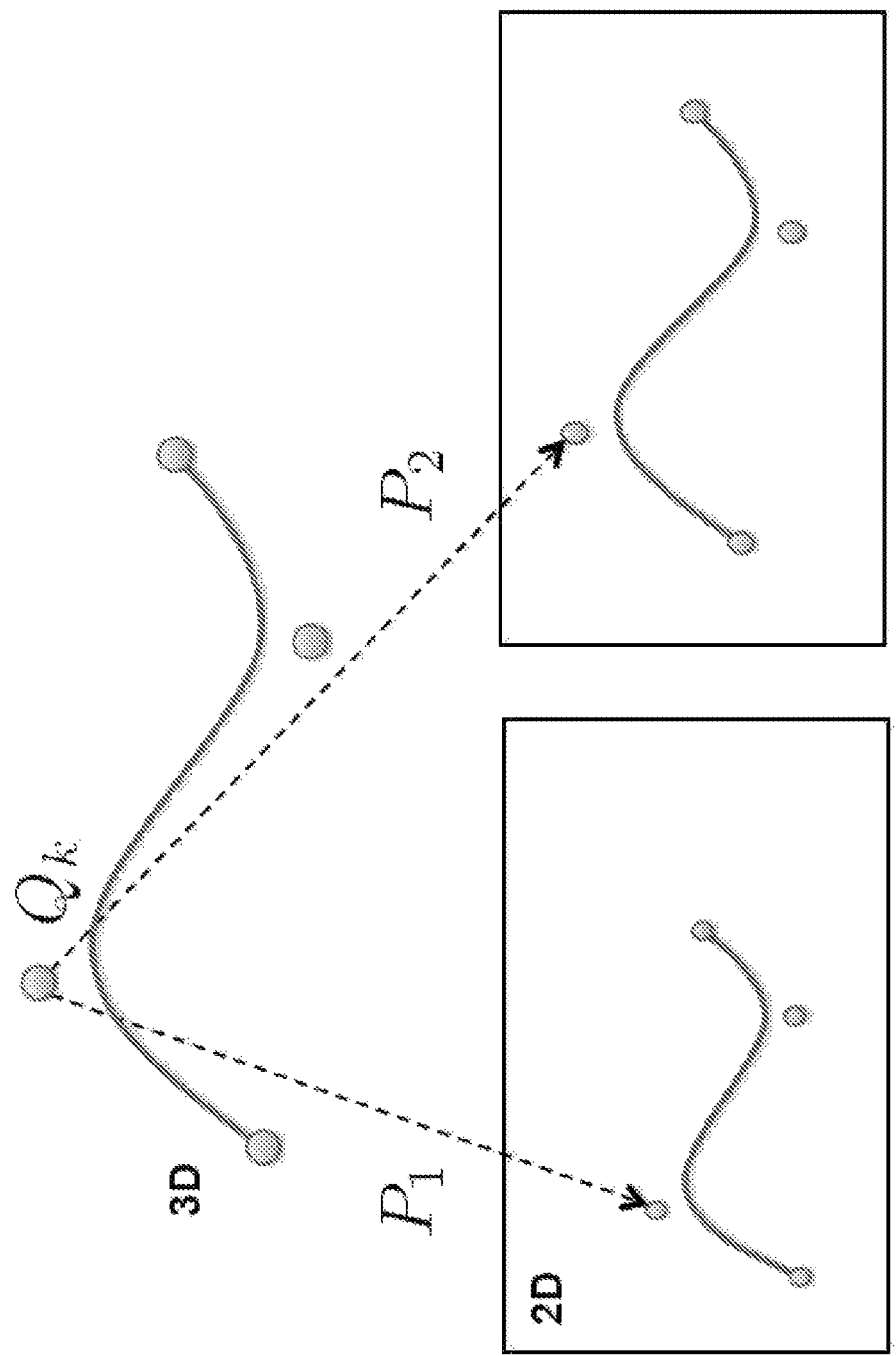
FIG. 2 illustrates the projection of the 3D NURBS curve on two images from the control points.

In other words, the projected 2D curves are the curves defined by the projected control points (see FIG. 2) and the appropriate weights $V_i=\{v_{i,k}\}$. In the following, we name $C^{3D}$ the 3D curve that models the thread with control point set $Q^{3Di}$. Its projection on the two images are called $C_1^{2D}$ and $C_2^{2D}$ with control point sets $Q_1^{2D}$ and $Q_2^{2D}$ We also use the notation omitting the control points and the weights for better readability.

2) 1D texture representation: The color pattern is composed of multiple colors alternating along the thread and is represented by a general function associating the curve parameter u to its color:

$$c(u): u \in [0,1] \to S,$$

where S is a color space, for instance the RGB or the HSV space. For generality, we do not require the two cameras to possess the same color-calibrations, but maintain instead two representations of the texture by using two functions: $c_i$ with $i \in \{1,2\}$. The pattern representation is known in advance or to be learned from the first pair of stereo images.

Tracking Ambiguities

Figure 3A:
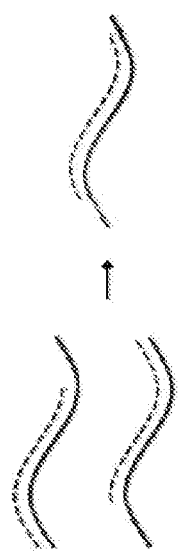
FIGS. 3A and 3B show examples of ambiguities resolved by the use of a 1D texture on the object.
Figure 3B:
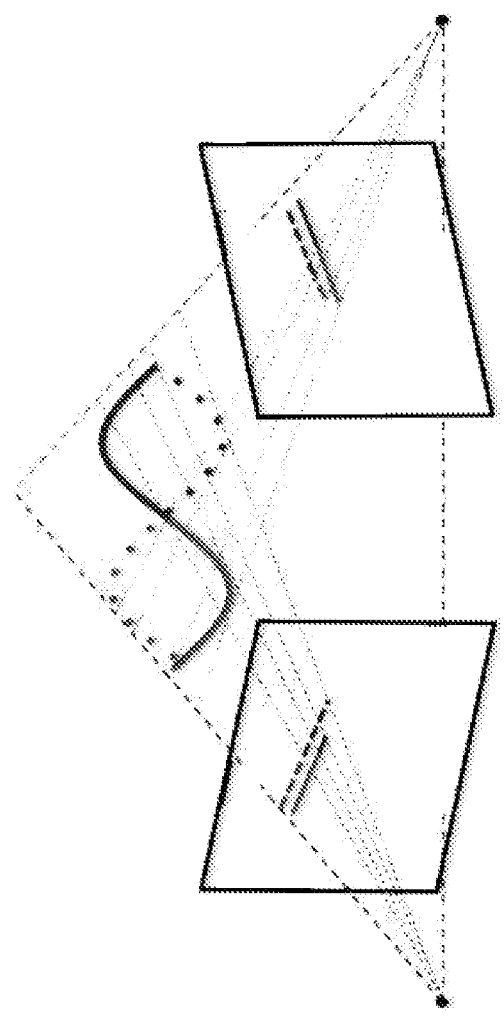

Using a mono-color thread, ambiguities occur when solely a part of the thread is tracked, or when a portion of the thread lies within an epipolar plane. The first ambiguous situation (FIG. 3A) is the most challenging one in practice, since it is generally difficult to obtain perfect initialization. The second situation occurs less commonly and can often be resolved by enforcing smoothness constraints in the object's deformations. FIGS. 3A and 3B illustrate two such situations where the pattern provides additional visual information that helps resolve the ambiguity. Other ambiguous situations are occlusions. Partial occlusions are coped with by enforcing the curvilinear, texture, length and smoothness constraints.

The discrete optimization method that we use also provides a large capture range allowing for quick recovery when the tracking is partially lost. To reduce the number of ambiguities, the pattern should ideally be chosen with several distinct colors and each unicolor portion of the pattern should be short. This way, multiple bendings will rarely occur on a unicolor portion as well as the aforementioned planar ambiguities.

Tracking Approach

Tracking the thread implies recovering, at each time step, the optimal parameters of the curve $C^{3D}$ so that its projections $\{C_1^{2D}\}$ match the thread visible in the stereo input images $I_1$ and $I_2$. In order to deal with noisy images and to resolve ambiguities, additional regularization constraints are also enforced. In curve tracking, the computation of the maximum a-posteriori estimate of the parameters based on the information from the input images is usually reformulated as an energy minimization problem [8], as done below.

1) Energy: The energy is defined as a sum of an external energy term, also called data term, driving the curve to its position observed by the images, and of an internal energy term providing curve regularization:

$$E = E_{ext} + \lambda E_{int} \quad (4)$$

$\lambda > 0$ is a parameter weighting the influence of the two terms. We define the external energy as a symmetric stereo projection error:

$$E_{ext} = \frac{1}{2} \sum_{i=1}^{2} \int_0^1 H_i(P_i(C^{3D}(\underline{\cdot}), \mathcal{W}, u))) du \quad (5)$$

$$= \frac{1}{2} \sum_{i=1}^{2} \int_0^1 H_i(C_i^{2D}(u)) du \quad (6)$$

where $\{H_i\}$ are cost functions penalizing projected curve points if they do not lie on the object in the images $I_i$.

Two fundamental properties of the object are used to evaluate the projected points: a projected point should lie within a ridge in the image (since the object has a tubular structure) and project on an image point whose color corresponds to the color of the pattern at its curve parameter u. The penalty functions $H_i$ is therefore composed of two terms:

$$H_i = \gamma_1 F_i + \gamma_2 G_i,$$

where functions $F_i(C_i^{2D}(u))$ evaluates the tubular structure of point $C_i^{2D}(u)$ in image $I_i$ and function $G_i(C_i^{2D}(u))$ evaluates its closeness to the color pattern $c_i$, $\gamma_1$ and $\gamma_2$ are coefficients weighting the influence of each term.

Typically, F evaluates the "ridgeness" using a Frangi filter computed on image $I_i$, and G is a distance in color space S:

$$G_i(C_i^{2D}(u)) = \|c_i(u) - \bar{I}_i(C_i^{2D}(u))\|^2,$$

where $\bar{I}_i$ is a Gaussian smoothed version of the original image $I_i$. More information about the practical computation of F and G is given below.

The internal energy maintains desired curve properties using curve derivatives, such as constant length using the initial curve at time 0 as reference:

$$E_{int} = \int_0^1 \left(1 - \frac{\|C^{3D'}(u)\|}{\|C_{ref}^{3D'}(u)\|}\right)^2 du. \quad (7)$$

Since the spline modeling already provides curve smoothness, additional smoothness terms are usually not necessary.

2) Parameterization: The energy E is optimized with respect to the set of control points $Q^{3D}$ containing 3K parameters. Since the NURBS spline representation is redundant, we fix the weights $w_k$ of the 3D curve to 1. But by updating the weights $v_{i,k}$ of the 2D curves according to eq. 3, one obtains a convenient parameterization of the 2D projections.

One should note that it is also possible to use a 2D-based parameterization, as done e.g. in [4] for contours. E would then have to be optimized over 4K parameters, namely $Q_1^{2D}$ and $Q_2^{2D}$. An additional energy term would be needed to enforce the stereo constraint.

Discrete Optimization

We use a discrete optimization scheme [8] to optimize the continuous energy presented above. Each control point is associated with a discrete random variable that describes its space of allowed 3D local displacements. These displacements are then computed using MRF modeling and optimization.

Figure 4A:
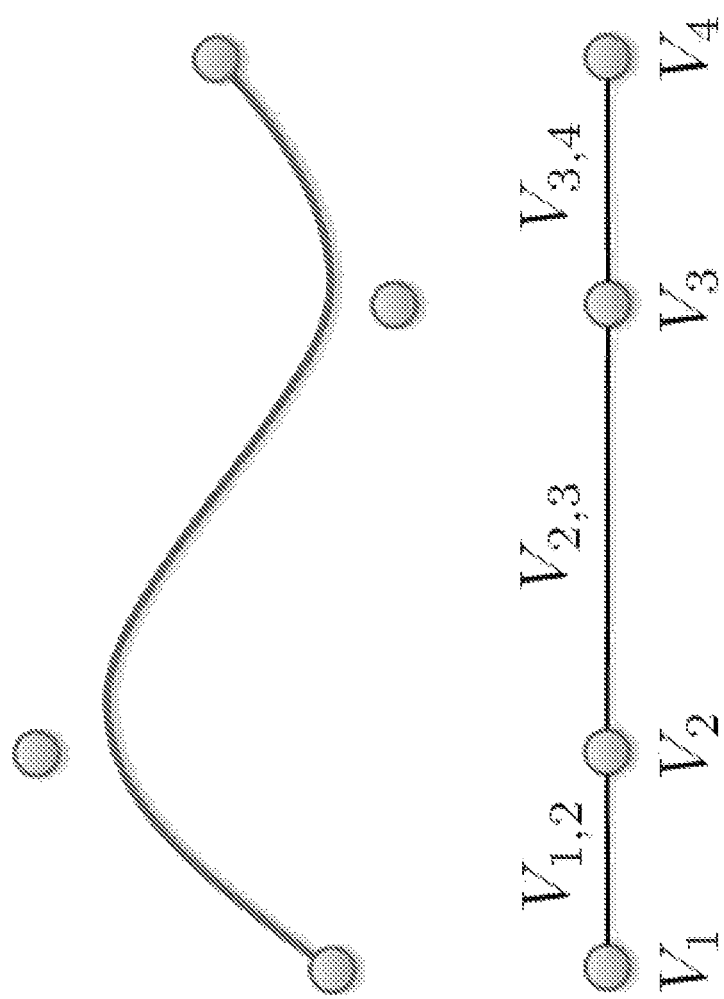
FIGS. 4A and 4B illustrate modeling of the control point optimization using a discrete MRF formulation.
Figure 4B:
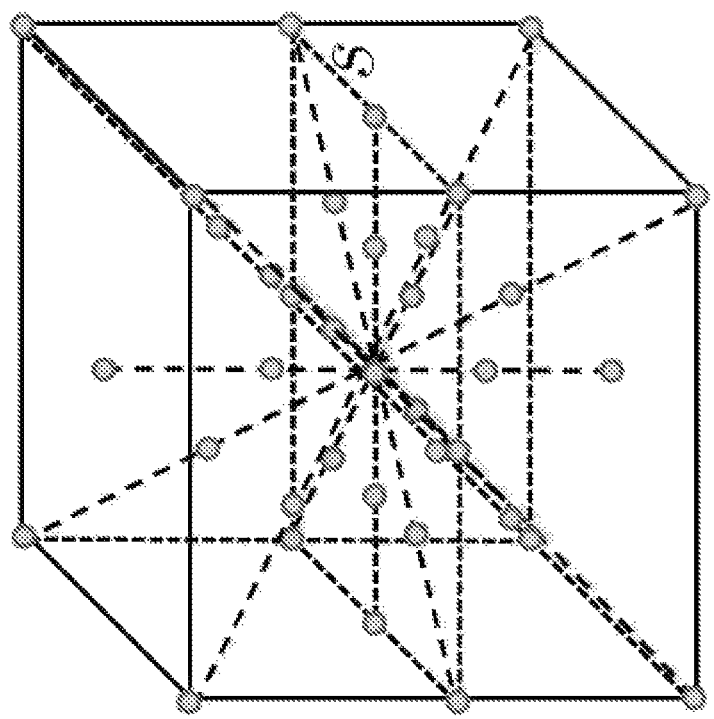

1) MRF modeling: Let (G;E) be a graph with a finite set of nodes G and set of edges E. Let also L be a discrete set of labels representing the search space. $x \in L$ represents a unique 3D displacement, as illustrated in FIG. 4B. The nodes G correspond to the control points and the edges connect pairs of nodes to model their inter-dependencies. If we assume dependencies only between pairs of neighboring control points when evaluating the energy, the graph is a chain, as illustrated in FIG. 4A. With this interpretation, tracking the curve is formulated as finding a label assignment $$G \to L,$$

$$p \in G \to l_p \quad (8)$$

associating each control point with a 3D displacement, such that the energy E is minimized. A first order Markov random field (MRF) [15] solves such labeling tasks by modeling and approximating the energy as a sum of unary and pairwise potentials:

$$E_{mrf} = \sum_{p \in G} V_p(l_p) + \lambda_1 \sum_{(p,q) \in E} V_{pq}(l_p, l_q). \quad (9)$$

The unary potentials $V_p$ evaluate the energy for each node p independently, while the pairwise potentials $V_{pq}$ evaluate the energy for pairs of inter-dependent nodes (p; q). In a spline of degree d, a point of the curve is affected by d+1 control points. For exact computation of the energy E, one should therefore consider sets of nodes (cliques) of size d+1. This can be formulated using higher order MRF. The computational cost of optimization methods for higher order MRF is however prohibitive for our application. We therefore approximate the exact energy E of eq. 4 by considering only unary and pairwise potentials. Our experiments will show that such approximations yield good results in practice.

2) Energy approximations: We consider two different approximations of E, both considering interdependencies between pairs of successive control points, using an MRF chain as shown in FIG. 4A. The first approximation $E_{mrf}^{(1)}$ models the data term and the length constraint with unary potentials. A third pairwise term is used for regularization in addition to the intrinsic spline smoothness, as done in [16]. We found by our experiments that this term improves the results when the inter-dependencies are neglected in the computation of the rest of the energy. The first approximation is expressed as $$E_{mrf}^{(1)} = \sum_{p \in G} (V_p^{(1a)}(l_p) + \lambda_1 V_p^{(1b)}(l_p)) + \lambda_2 \sum_{(p,q) \in E} V_{pq}^{(1c)}(l_p, l_q), \quad (10)$$

with $$V_p^{(1a)}(l_p) = \frac{1}{2} \sum_{i=1}^{2} \int_0^1 \alpha_p(u)(H_i(C_i^{2D}(\{l_p\}, u))) du \quad (11)$$

$$V_p^{(1b)}(l_p) = \int_0^1 \alpha_p(u) \left(1 - \frac{\|C^{3D'}(\{l_p\}, u)\|}{\|C_{ref}^{3D'}(u)\|}\right)^2 du \quad (12)$$

$$V_{pq}^{(1c)}(l_p, l_q) = \|l_p - l_q\|. \quad (13)$$

The notation $\{l_p\}$ indicates that the p-th control point of the 3D curve is modified by the 3D displacement $l_p$. $C_i^{2D}(\{l_p\}, u)$ is a point of the corresponding projected curve. The variables $\alpha_p(u)$ weight the influence of control point p over the curve point at position u and are obtained naturally from the basis functions:

The second approximation models the data term and the length constraint with pairwise potentials:

$$E_{mrf}^{(2)} = \sum_{(p,q) \in E} (V_{pq}^{(2a)}(l_p, l_q) + \lambda_1 V_{pq}^{(2b)}(l_p, l_q)), \quad (15)$$

with $$V_{pq}^{(2a)}(l_p, l_q) = \frac{1}{2} \sum_{i=1}^{2} \int_0^1 \alpha_{pq}(u) H_i(C_i^{2D}(\{l_p, l_q\}, u)) du \quad (16)$$

$$V_{pq}^{(2b)}(l_p, l_q) = \int_0^1 \alpha_{pq}(u) \left(1 - \frac{\|C^{3D'}(\{l_p, l_q\}, u)\|}{\|C_{ref}^{3D'}(u)\|}\right)^2 du. \quad (17)$$

As above, the notation $\{l_p, l_q\}$ indicates that the p-th control point is modified by the displacement and the q-th control point is modified by displacement $l_q$. $C_i^{2D}(\{l_p, l_q\}, u)$ is a point of the corresponding projected curve and the variables $\alpha_{pq}(u)$ weight the influence of the two control points over the curve point at position u. They are defined by the product model from [8]:

$$\alpha_{pq}(u) = \frac{R_p(u) R_q(u)}{\sum_{k=1}^{K-1} R_k(u) R_{k+1}(u)}. \quad (18)$$

3) Optimization: To solve the aforementioned discrete MRF formulation, we use the FastPD algorithm [17]. This is a computationally efficient approach based on linear programming which has shown good real-time performance for 2D tracking [8]. In practice, note that $E_{mrf}^{(1)}$ is faster to optimize than the more precise energy $E_{mrf}^{(2)}$, since the pairwise evaluations are less time-consuming. The efficiency of the optimization is also driven by the sizes of G and L. Due to the large 3D search space, we use a sparse set of labels L(r, s) sampling seven 3D directions (top-down, left-right, front-back and the four main cube diagonals). L(r, s) depends on two parameters: r, the number of labels in each oriented direction and s, the 3D distance between two consecutive labels in the top-down direction. The possible 3D displacements for r=2 are indicated in FIG. 4B. L(r, s) contain (14r+1) labels that sparsely sample a cube of side length (2rs) mm.

The parameters r and s constitute a trade-off between speed and optimization quality. For a fixed r, we therefore adapt the parameter s at each tracking step based on the amount of motion estimated from the images. The optical flow is computed sparsely along the spline in both images and triangulated (or scaled using the average depth of the thread and the known focal length in a mono-camera scenario). The average intensity (norm) of 3D motion along the spline is then estimated using a robust median estimator and s is chosen so that $$\frac{sr}{2} = \bar{m}.$$

This choice covers a search space likely to encompass the amount of displacements undergone by the thread.

Gradient-Based Optimization

In this approach, E is optimized with respect to the set of control points $Q^{3D}$ using a gradient-based approached such as gradient-descent or the Levenberg-Marquardt algorithm. Since the object is tubular, the images contain high-frequency components around the thread location. To obtain a smooth energy suitable for gradient-based optimization, a key step in this approach is to smoothen the image before the computation of the image derivatives $$\frac{\partial I_i}{\partial xy},$$

occurring during the derivation of the data term

Data Term

Figure 5:
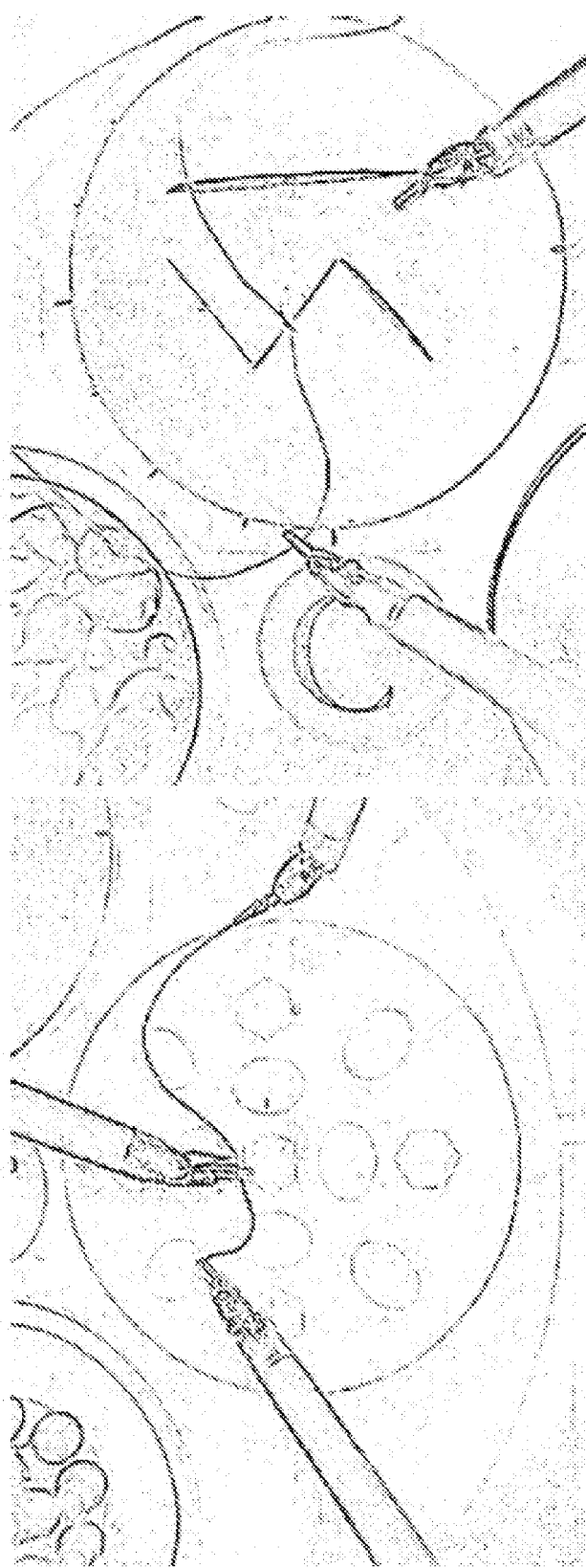
FIG. 5 shows outputs of the curvilinear detector used to compute the cost images.

The penalty function $F_i$ is defined using a Frangi filter [18] that detects the curvilinear structures in image L by analyzing the Hessian matrix at each image locations. Outputs of this detector can be seen in FIG. 5. To define $F_i$, this detection is further thresholded and processed with a Euclidean distance transform in order to create smooth $G_i(C_i^{2D}(u)) = \|c_i(u) - \bar{I}_i(C_i^{2D}(u))\|^2$ borders along the detected ridges. The second penalty function enforces the color constraints, using a Gaussian smoothened version $\bar{I}_i$ of the original image $I_i$, Tracking of Curve Extremities Curve extremities are more difficult to track than the rest of the thread, since they are subject to fewer constraints. Therefore, if instruments with known positions are used to manipulate the thread extremities, their position information can be used as an additional energy term to further constrain the tracking. Since the measurements are often approximate, we use the following soft constraint as unary energy term:

$$E_{tips} = \|C^{3D}(0) - T_0\|_\epsilon + \|C^{3D}(1) - T_1\|_\epsilon, \quad (19)$$

where $T_0$ and $T_1$ are the measured extremity locations. $\|x\|_\epsilon$ is 0 if $\|x\| \leq \epsilon$ and the usual norm $\|x\|$ otherwise.

EXPERIMENTS

Figure 7:
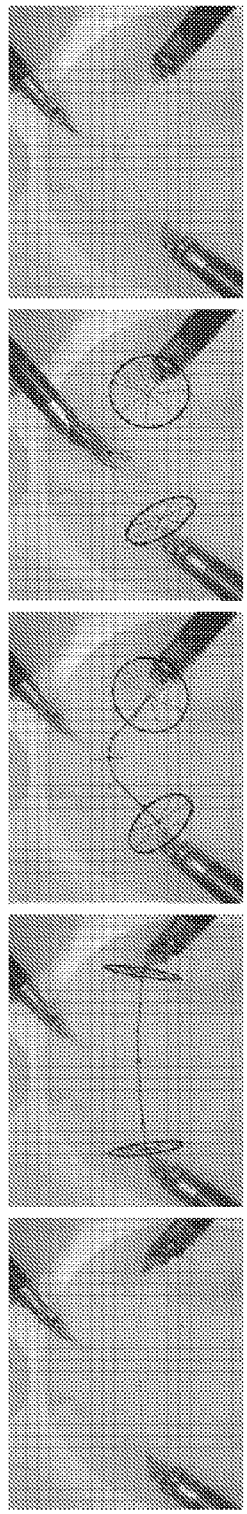
FIG. 7 is an example of automatic thread cutting by a third instrument with an automatic scissors command, using a unicolor thread and tool position information according to an embodiment of the current invention.

Previous synthetic and real experiments on a unicolor thread using solely the curvilinear, length and tool extremity constraints are available in [13]. They are illustrated in FIG. 6. Illustrations of the automatic scissor command, where the third robotic arm comes and cuts the tracked thread automatically in its center, are provided in FIG. 7.

Figure 8:
FIG. 8 shows synthetic tracking results using a thread textured with a bicolor pattern (blurred original image is shown under the projected model).
Figure 9:
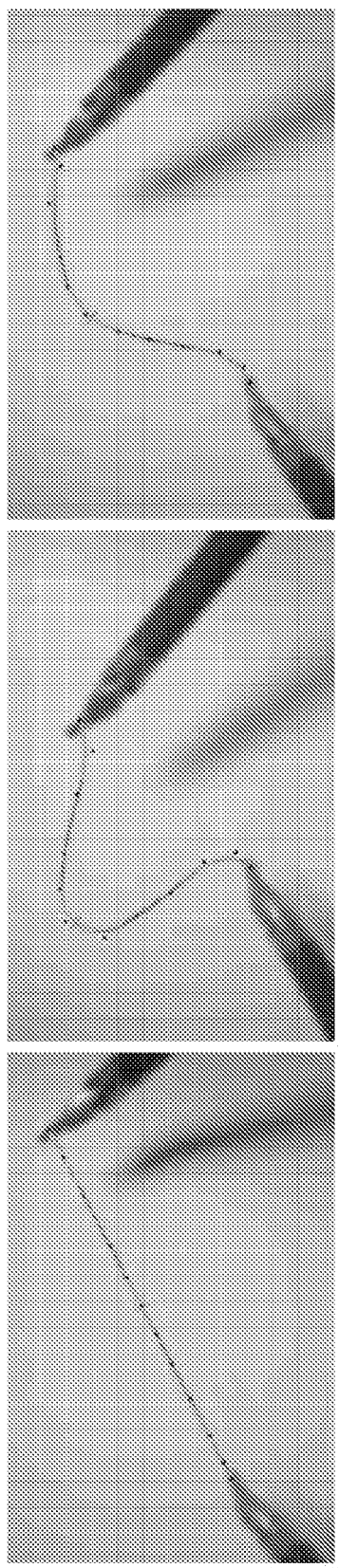
FIG. 9 shows real tracking results using a thread textured with a bicolor pattern (blurred original image is shown under the projected model) according to an embodiment of the current invention.

FIG. 8 shows an illustration of a tracking approach on synthetic images generated using a synthetic thread with a bicolor pattern. FIG. 9 shows illustrations of real tracking experiments. In the experimental setup, the thread is telemanipulated using a da Vinci surgical robot and observed by a stereo endoscopic camera (Ikegami HD), as shown in FIG. 1. The curves are cubic splines with a fixed number ten control points. In the energies, we use a large weight $\lambda$ for the length constancy constraint, and weight equally the curvilinear and texture terms. No tool information is used. We assume the splines to be initialized at the beginning of the tracking, for instance by providing the extremity locations and running a few iterations of the optimization on a spline initially defined as a straight line. During the tracking shown in these pictures, we use discrete optimization with energy approximations $E_{mrf}^{(I)}$ and perform two optimization steps with two label sets $L(r,s)$ and $$L\left(r, \frac{s}{2}\right)$$

at each image frame.

DISCUSSION AND CONCLUSION

To apply embodiments to robotic assistance systems that require automatic thread manipulation, the exact position of the thread should be known. A thread is however a highly deformable curvilinear structure, which can undergo large deformations and displacements. To address ambiguous situations, texture of the thread, such as a color pattern can be included. An approach based on discrete optimization for the thread tracking from stereo can also be used in some applications. We model the 3D thread as well as its 2D projections with nonuniform rational B-splines in some embodiments. We then embed the parameter optimization in a discrete Markov random field optimization framework that provides a large tracking capture range. Two discrete approximations of the global energy are also provided. Finally, we illustrated the approach with tracking experiments on synthetic and real data. In particular, we demonstrated our approach for an automatic scissors command during tele-surgery.

REFERENCES

[1] M. Kass, A. P. Witkin, and D. Terzopoulos, "Snakes: Active contour models," IJCV, vol. 1, no. 4, pp. 321-331, 1988.

[2] D. Geiger, A. Gupta, L. A. Costa, and J. Vlontzos, "Dynamic programming for detecting, tracking, and matching deformable contours," PAMI, vol. 17, no. 3, pp. 294-302, 1995.

[3] A. A. Amini, R. W. Curwen, and J. C. Gore, "Snakes and splines for tracking non-rigid heart motion," in ECCV, 1996, pp. 251-261.

[4] T.-J. Cham and R. Cipolla, "Stereo coupled active contours," Computer Vision and Pattern Recognition, IEEE Computer Society Conference on, vol. 0, p. 1094, 1997.

[5] M. Isard and A. Blake, "Condensation—conditional density propagation for visual tracking," IJCV, vol. 29, no. 1, pp. 5-28, 1998.

[6] G. Shechter, F. Devernay, E. Coste Mani'ere, and E. Mcveigh, "Temporal tracking of 3D coronary arteries in projection angiograms," in Medical Imaging, vol. 4684. SPIE, 2002.

[7] P. Wang, T. Chen, Y. Zhu, W. Zhang, S. K. Zhou, and D. Comaniciu, "Robust guidewire tracking in fluoroscopy," in CVPR, 2009, pp. 691-698.

[8] T. H. Heibel, B. Glocker, M. Groher, N. Paragios, N. Komodakis, and N. Navab, "Discrete tracking of parametrized curves," in CVPR, 2009.

[9] H. G. Mayer, F. J. Gomez, D. Wierstra, I. Nagy, A. Knoll, and J. Schmidhuber, "A system for robotic heart surgery that learns to tie knots using recurrent neural networks," in IROS, 2006, pp. 543-548.

[10] J. van den Berg, S. Miller, D. Duckworth, H. Hu, A. Wan, X.-Y. Fu, K. Goldberg, and P. Abbeel, "Superhuman performance of surgical tasks by robots using iterative learning from human-guided demonstrations," in ICRA, 2010, pp. 2074-2081.

[11] A. Bartoli, M. Perriollat, and S. Chambon, "Generalized thin-plate splinewarps," in CVPR, 2007.

[12] S. Javdani, S. Tandon, J. Tang, J. F. O'Brien, and P. Abbeel, "Modeling and perception of deformable one-dimensional objects," in ICRA, 2011, pp. 1607-1614.

[13] N. Padoy and G. D. Hager, "3d thread tracking for robotic assistance in tele-surgery," in IROS, 2011, pp. 2102-2107.

[14] L. Piegl and W. Tiller, The Nurbs Book, 2nd ed. Springer, 1997.

[15] S. Z. Li, Markov random field modeling in image analysis. Springer-Verlag New York, Inc., 2001.

[16] B. Glocker, N. Komodakis, G. Tziritas, N. Navab, and N. Paragios, "Dense image registration through mrfs and efficient linear programming," Medical Image Analysis, vol. 12, no. 6, pp. 731-741, 2008.

[17] N. Komodakis, G. Tziritas, and N. Paragios, "Fast, approximately optimal solutions for single and dynamic mrfs," in CVPR, 2007.

[18] A. F. Frangi, W. J. Niessen, K. L. Vincken, and M. A. Viergever, "Muliscale vessel enhancement filtering," in MICCAI, 1998, pp. 130-137.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A system for detecting and tracking a curvilinear object in a three-dimensional space, comprising:
   an image acquisition system comprising a video camera arranged to acquire a video image of said curvilinear object and output a corresponding video signal, said video image comprising a plurality n of image frames each at a respective time $t_i$, where i=1, 2, . . . , n; and
   a data processing system adapted to communicate with said image acquisition system to receive said video signal,
   wherein said data processing system is configured to determine a position, orientation and shape of said curvilinear object in said three-dimensional space at each time $t_i$ by forming a computational model of said curvilinear object at each time $t_i$ such that a projection of said computation model of said curvilinear object at each time $t_i$ onto a corresponding frame of said plurality of image frames of said video image matches a curvilinear image in said frame to a predetermined accuracy to thereby detect and track said curvilinear object from time $t_1$ to time $t_n$.

2. A system for detecting and tracking a curvilinear object in a three-dimensional space according to claim 1, wherein said computational model is a non-uniform rational B-spline model.

3. A system for detecting and tracking a curvilinear object in a three-dimensional space according to claim 1, wherein said image acquisition system a depth camera.

4. A system for detecting and tracking a curvilinear object in a three-dimensional space according to claim 1, wherein said curvilinear object comprises a texture that is visible in said video image and said data processing system is further configured to determine said texture of said curvilinear object in said three-dimensional space at each time $t_i$ by including texture in said computational model of said curvilinear object at each time $t_i$.

5. A system for detecting and tracking a curvilinear object in a three-dimensional space according to claim 4, wherein said texture is a color pattern such that some portions of said curvilinear object are distinguishable from other portions based on differences in color.

6. A system for detecting and tracking a curvilinear object in a three-dimensional space according to claim 1, wherein said curvilinear object has a substantially invariant length and said computational model of said curvilinear object includes a constant-length constraint on the modeled curvilinear object.

7. A system for detecting and tracking a curvilinear object in a three-dimensional space according to claim 1, wherein said video camera is a stereo video camera arranged to acquire a stereo video image of said curvilinear object and output a corresponding stereo video signal, said stereo video image comprising a plurality n stereo pairs of image frames each at a respective time $t_i$ where i=1, 2, . . . , n,
   wherein said data processing system is adapted to communicate with said image acquisition system to receive said stereo video signal,
   wherein said data processing system is configured to determine a position, orientation and shape of said curvilinear object in said three-dimensional space at each time $t_i$ by forming a computational model of said curvilinear object at each time $t_i$ such that a projection of said computation model of said curvilinear object at each time $t_i$ onto a corresponding stereo pair of frames of said plurality of stereo pairs of image frames of said stereo video image matches a two-dimensional curvilinear image in said stereo pair of frames to a predetermined accuracy to thereby detect and track said curvilinear object from time $t_1$ to time $t_n$.

8. A method for detecting and tracking a curvilinear object in a three-dimensional space, comprising:
   receiving, by a data processing system, a video signal from an image acquisition system that comprises a video camera arranged to acquire a video image of said curvilinear object and output said video signal, said video image comprising a plurality n of image frames each at a respective time $t_i$, where i=1, 2, . . . , n; and
   determining a position, orientation and shape of said curvilinear object in said three-dimensional space at each time $t_i$ by forming a computational model of said curvilinear object at each time $t_i$ using said data processing system such that a projection of said computation model of said curvilinear object at each time $t_i$ onto a corresponding frame of said plurality of image frames of said video image matches a curvilinear image in said frame to a predetermined accuracy to thereby detect and track said curvilinear object from time $t_1$ to time $t_n$.

9. A method for detecting and tracking a curvilinear object in a three-dimensional space according to claim 8, wherein said computational model is a non-uniform rational B-spline model.

10. A method for detecting and tracking a curvilinear object in a three-dimensional space according to claim 8, wherein said curvilinear object comprises a texture that is visible in said video image and said data processing system is further configured to determine said texture of said curvilinear object in said three-dimensional space at each time $t_i$ by including texture in said computational model of said curvilinear object at each time $t_i$.

11. A method for detecting and tracking a curvilinear object in a three-dimensional space according to claim 10, wherein said texture is a color pattern such that some portions of said curvilinear object are distinguishable from other portions based on differences in color.

12. A method for detecting and tracking a curvilinear object in a three-dimensional space according to claim 8, wherein said curvilinear object has a substantially invariant length and said computational model of said curvilinear object includes a constant-length constraint on the modeled curvilinear object.

13. A method for detecting and tracking a curvilinear object in a three-dimensional space according to claim 8, wherein said video camera is a stereo video camera arranged to acquire a stereo video image of said curvilinear object and output a corresponding stereo video signal, said stereo video image comprising a plurality n stereo pairs of image frames each at a respective time $t_i$ where i=1, 2, . . . , n,
   wherein said determining a position, orientation and shape of said curvilinear object in said three-dimensional space comprises determining a position, orientation and shape of said curvilinear object in said three-dimensional space at each time $t_i$ by forming a computational model of said curvilinear object at each time $t_i$ such that a projection of said computation model of said curvilinear object at each time $t_i$ onto a corresponding stereo pair of frames of said plurality of stereo pairs of image frames of said stereo video image matches a two-dimensional curvilinear image in said stereo pair of frames to a predetermined accuracy to thereby detect and track said curvilinear object from time $t_1$ to time $t_n$.

14. A non-transitory computer-readable medium comprising computer-executable code for detecting and tracking a curvilinear object in a three-dimensional space, said computer-executable code comprising instructions that, when executed by said computer, causes said computer to:
receive a video signal from an image acquisition system that comprises a video camera arranged to acquire a video image of said curvilinear object and output said video signal, said video image comprising a plurality n of image frames each at a respective time $t_i$, where i=1, 2, . . . , n; and
determine a position, orientation and shape of said curvilinear object in said three-dimensional space at each time $t_i$ by forming a computational model of said curvilinear object at each time $t_i$ such that a projection of said computation model of said curvilinear object at each time $t_i$ onto a corresponding frame of said plurality of image frames of said video image matches a curvilinear image in said frame to a predetermined accuracy to thereby detect and track said curvilinear object from time $t_1$ to time $t_n$.

15. The non-transitory computer-readable medium according to claim 14, wherein said computational model is a non-uniform rational B-spline model.

16. The non-transitory computer-readable medium according to claim 14, wherein said curvilinear object comprises a texture that is visible in said video image and said data processing system is further configured to determine said texture of said curvilinear object in said three-dimensional space at each time $t_i$ by including texture in said computational model of said curvilinear object at each time $t_i$.

17. The non-transitory computer-readable medium according to claim 16, wherein said texture is a color pattern such that some portions of said curvilinear object are distinguishable from other portions based on differences in color.

18. The non-transitory computer-readable medium according to claim 14, wherein said curvilinear object has a substantially invariant length and said computational model of said curvilinear object includes a constant-length constraint on the modeled curvilinear object.

19. The non-transitory computer-readable medium according to claim 14, wherein said video camera is a stereo video camera arranged to acquire a stereo video image of said curvilinear object and output a corresponding stereo video signal, said stereo video image comprising a plurality n stereo pairs of image frames each at a respective time $t_i$, where i=1, 2, . . . , n,
wherein said determining a position, orientation and shape of said curvilinear object in said three-dimensional space comprises determining a position, orientation and shape of said curvilinear object in said three-dimensional space at each time $t_i$ by forming a computational model of said curvilinear object at each time $t_i$ such that a projection of said computation model of said curvilinear object at each time $t_i$ onto a corresponding stereo pair of frames of said plurality of stereo pairs of image frames of said stereo video image matches a two-dimensional curvilinear image in said stereo pair of frames to a predetermined accuracy to thereby detect and track said curvilinear object from time $t_i$ to time $t_n$.

* * * * *